United States Patent
Rhodes et al.

(10) Patent No.: US 6,971,258 B2
(45) Date of Patent: Dec. 6, 2005

(54) PARTICULATE MATTER SENSOR

(75) Inventors: Michael L. Rhodes, Richfield, MN (US); Brian C. Krafthefer, Stillwater, MN (US); Hongbin Ma, Falcon Heights, MN (US); David B. Kittelson, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/749,498

(22) Filed: Dec. 31, 2003

(65) Prior Publication Data

US 2005/0145023 A1    Jul. 7, 2005

(51) Int. Cl.[7] .............................................. G01N 37/00
(52) U.S. Cl. ..................................... 73/28.01; 73/28.02
(58) Field of Search ............................... 73/28.01, 28.02

(56) References Cited

U.S. PATENT DOCUMENTS

| | | | | |
|---|---|---|---|---|
| 4,307,061 A | * | 12/1981 | Sarholz ........................ 422/94 |
| 4,485,794 A | * | 12/1984 | Kimberley et al. .......... 123/681 |
| 5,076,237 A | | 12/1991 | Hartman et al. | |
| 5,180,983 A | * | 1/1993 | Murata et al. ............... 324/399 |
| 5,681,986 A | * | 10/1997 | Merk et al. ................. 73/61.75 |
| 5,898,257 A | * | 4/1999 | Sequerra et al. ............. 313/141 |
| 6,192,740 B1 | | 2/2001 | Fredrick et al. | |
| 6,341,501 B2 | * | 1/2002 | Sugimoto et al. ............. 65/32.2 |
| 6,466,022 B1 | * | 10/2002 | Koopmans .................... 324/399 |
| 6,512,375 B1 | * | 1/2003 | Yamada et al. .............. 324/399 |
| 6,583,539 B1 | * | 6/2003 | Zamora ........................ 313/143 |
| 6,634,210 B1 | | 10/2003 | Bosch et al. | |
| 2003/0234012 A1 | * | 12/2003 | Bosteels ...................... 123/670 |

FOREIGN PATENT DOCUMENTS

| | | | | |
|---|---|---|---|---|
| DE | 19536705 | | 4/1997 | |
| DE | 19853841 | | 6/1999 | |
| DE | 10128869 A1 | * | 1/2002 | |
| EP | 0353196 | | 1/1990 | |
| JP | 60039543 A | * | 3/1985 | ................. 73/28.01 |
| JP | 60123761 A | * | 7/1985 | ................. 73/28.02 |

OTHER PUBLICATIONS

Abstract for JP 60100046 A to Maeda, Shoji.*

* cited by examiner

*Primary Examiner*—Michael Cygan
(74) *Attorney, Agent, or Firm*—Kris Fredrick

(57) ABSTRACT

A sensor for detecting particulate matter in an exhaust stream of an engine. The sensor may be a spark-plug-like device having an extended center electrode composed of a stainless steel or other material. The electrode may have a thin passivating layer formed on it. The layer may be grown or deposited on the electrode within the exhaust system. The sensor may detect charge transients indicative of particulate concentration in the exhaust stream. Information about particulate matter in the exhaust system along with other engine information may be processed for controlling or adjusting parameters of the engine to affect the particulate matter in the exhaust system.

20 Claims, 6 Drawing Sheets

PARTICULATE MATTER SENSOR

This invention was made with government support under B09380012 awarded by Honeywell International, Inc. (DOE Prime #DE-FC 04-02AL67636). The government has certain rights in the invention.

BACKGROUND

The present invention pertains to sensors and particularly to sensing particles in the air. More particularly, the invention pertains to sensing emissions.

Many combustion devices produce particulate emissions. For example, diesel engines are increasing in popularity in many kinds of vehicles. In the meanwhile, environmental regulations relative to particulate emissions are becoming more stringent. Thus, there is need for minimizing emissions from diesel engines and other particulate emitting mechanisms.

SUMMARY

The present invention is a sensor for detecting and monitoring particulate emissions. The sensor outputs a signal indicating an amount of such emissions. The signal may be sent to a processor or controller that outputs a control signal indicative of the amount of emissions. This signal may be sent to a controller of mechanism expelling the emissions to minimize the output of the emissions.

DESCRIPTION

Figure 1:
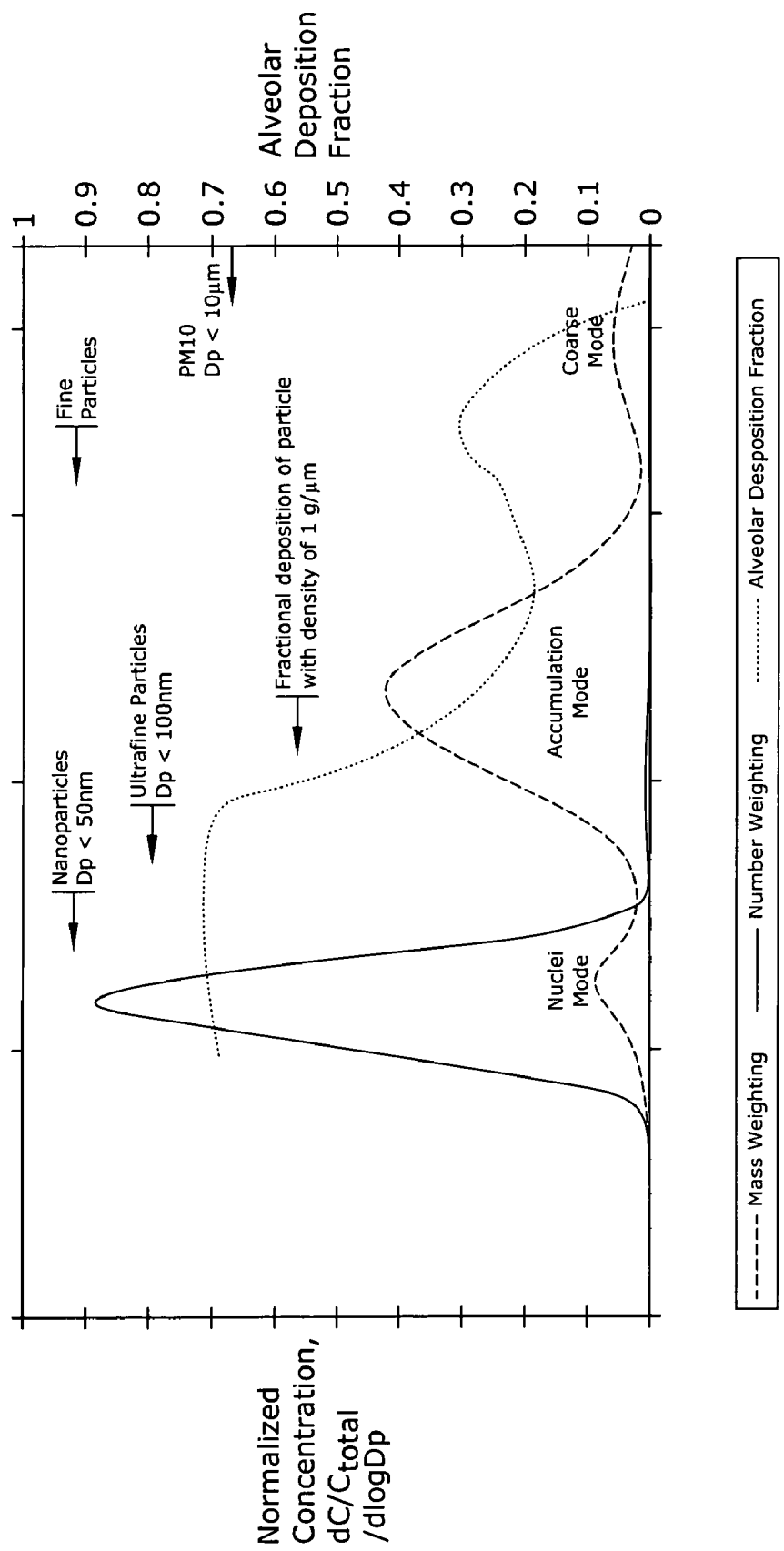
FIG. 1 is a graph showing typical engine exhaust mass and number weighted size distributions shown with Alveolar deposition.

FIG. 1 is a graph showing engine exhaust and the number of weighted size distributions shown with an alveolar deposition fraction. The graph illustrates an idealized diesel particulate matter (PM) number and mass weighted distribution. The PM follows a lognormal, trimodal size distribution with the concentration in any size range being proportional to the area under the corresponding curve in that range. The nuclei mode particles range in diameter from 0.005 to 0.05 micron (5–50 nm). They consist of metallic compounds, elemental carbon and semivolatile organic and sulfur compounds that form particles during exhaust dilution and cooling. The nuclei mode typically contains 1 to 20 percent of the particle mass and more than 90 percent of the particle number. The accumulation mode particles range in diameter from 0.05 to 0.5 micron (50 to 500 nm). Most of the mass, composed primarily of carbonaceous agglomerates and adsorbed materials, is found here. The course mode consists of particles larger than one micron in diameter and contains 5 to 20 percent of the PM mass. These relatively large particles are formed by re-entrainment of particulate matter, which has been deposited on cylinder and exhaust system surfaces.

PM emissions contribute to the fine particle burden in the atmosphere, and the EPA has established a light-duty vehicle PM emission standard of 0.08 g/mile and has promulgated a regulation to limit the amount of particular matter with a diameter of 2.5 microns or less (such as the newer 0.1 micron standard being considered). To meet these standards, engine manufacturers have developed low-emission engines. Technological improvements may have reduced mass emissions, but it has been said the newer engines meeting the 1991 emissions limit requirements had dramatically increased numbers and volumes of very small nuclei mode particles when compared to similar engines meeting 1988 emissions limit requirements. These observations suggest that not only accumulation mode size particles, but also nuclei mode size particles, may pose future emission problems.

Particles in the nuclei mode and in the accumulation mode appear to be formed by different mechanisms. Accumulation mode particles are primarily carbonaceous and are associated with rich combustion and poor subsequent oxidation during the engine cycle. On the other hand, most nuclei mode particles are not even formed until the exhaust combustion products dilute and cool. They consist of a complex, poorly understood mix of sulfuric acid and particularly burned fuel and lubricating oil. Formation of these two types of particles likely occurs under different engine operating conditions. One condition is heavy loads favoring carbonaceous accumulation mode particles. Another condition is light loads most likely favoring the formation of vapor phase precursors of nuclei mode particles. The precursors may not undergo gas to particle conversion until the exhaust cools and dilutes in the atmosphere.

In order to meet future emission standards, diesel engines need to be fitted with combustion control systems. Also, an after treatment system including particle filters or traps will be needed. To make such combustion control systems and after treatment devices reasonably feasible to reduce particulate emissions from an engine, an effective exhaust particulate sensor is needed.

Particulate traps are available but they are large, expensive and significantly reduce fuel economy. The reduction in fuel economy is due to additional back pressure in the exhaust system being applied to the engine.

Figure 4:
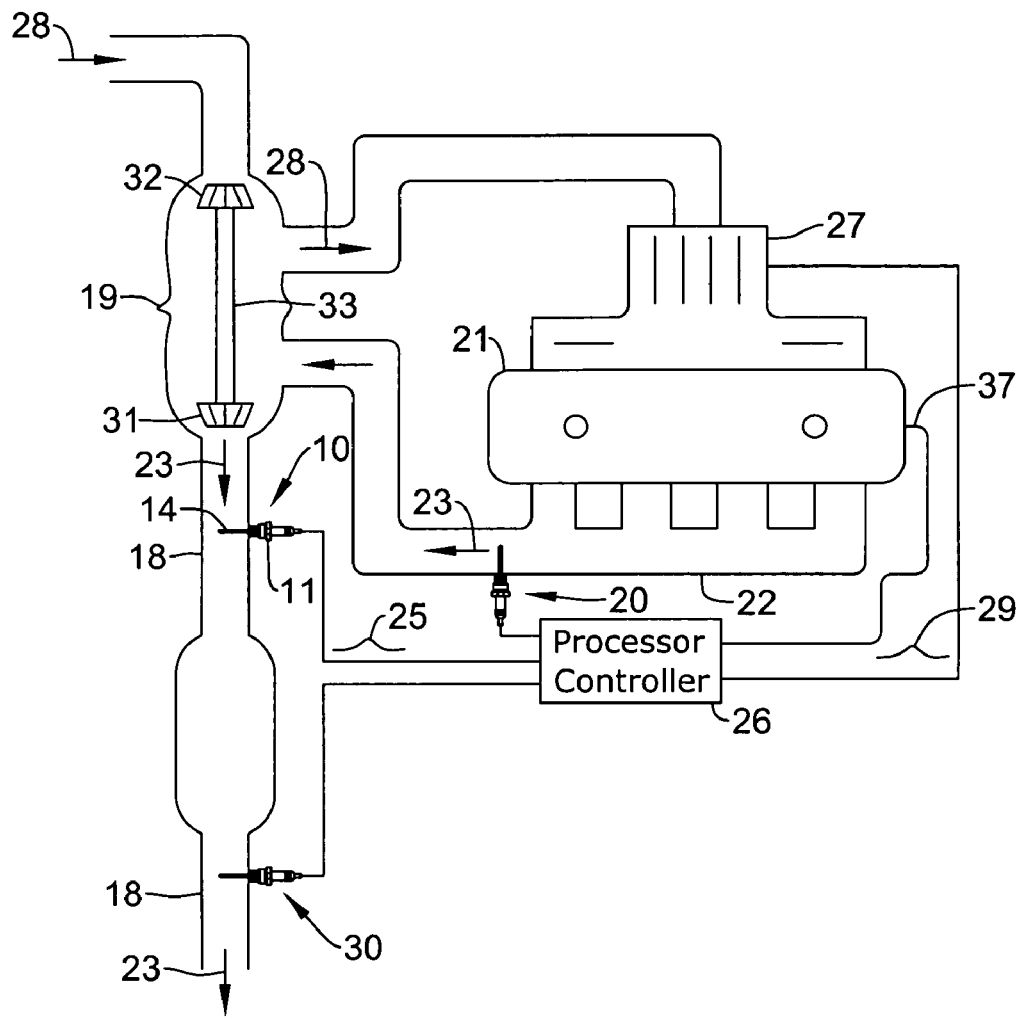
FIG. 4 shows an implementation of the PM sensor in an engine.

The present sensor 10 may be built upon an automotive spark plug 11. To obtain a very good high temperature and a high pressure platform for the sensor, the sensor may be placed directly in the engine's exhaust pipe 18, manifold or header 22. If the engine 21 has a turbocharger 19, as in FIG. 4, then the sensor 10 may be placed downstream from the turbocharger 19 to avoid harm to the turbocharger if sensor 10 releases some particles.

Figure 2:
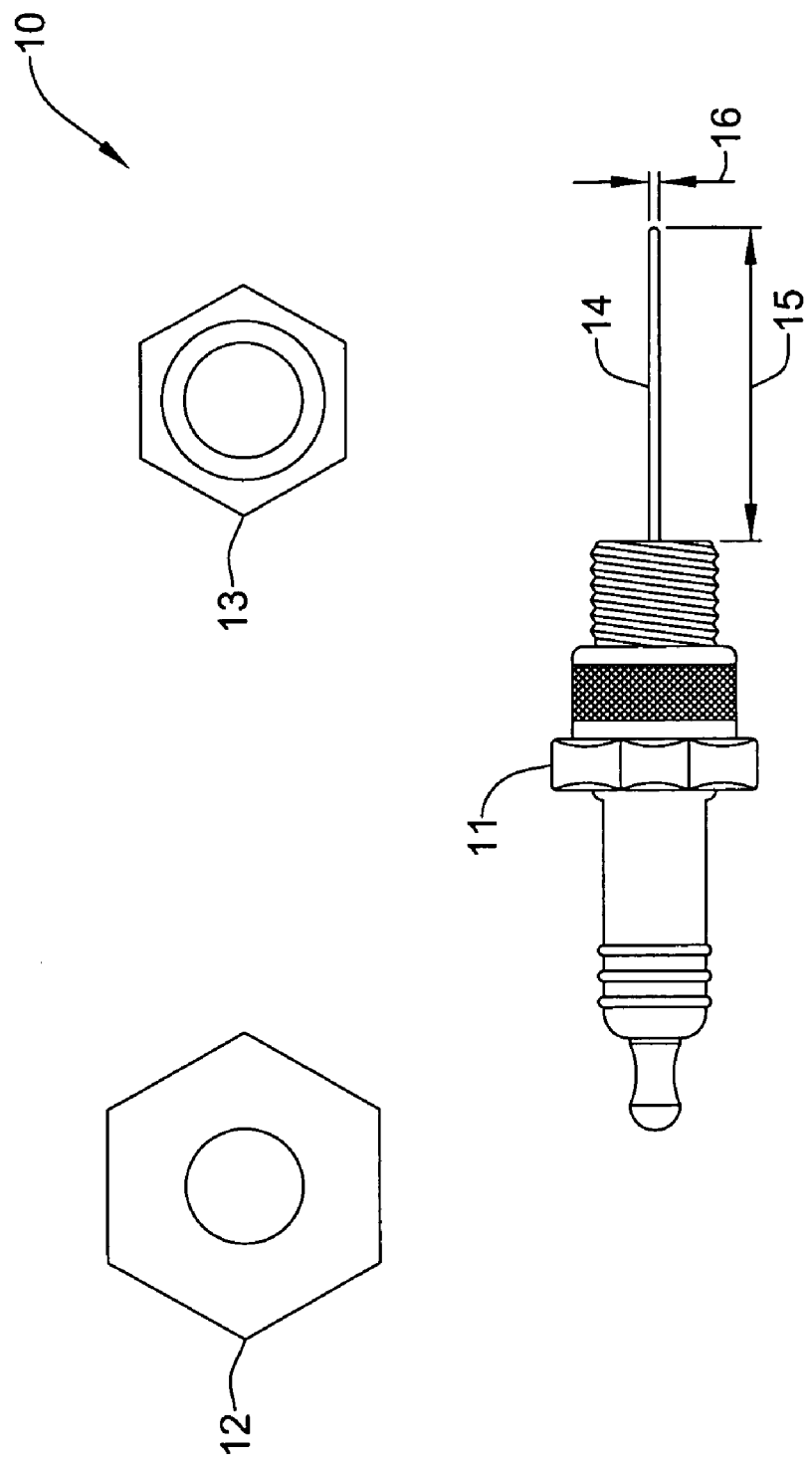
FIG. 2 reveals basic components of the particulate matter (PM) sensor.

The design of the sensor 10 may provide for low cost and high volume manufacturing of the sensor. The sensor design, as in FIG. 2, may use Swageloc™, fittings 12 and/or fabricated high temperature ceramic feed-through insulators 13 and/or connectors. A probe 14 of sensor 10 may be placed in the path of the exhaust of the engine. The length 15 and diameter 16 of probe 14 may be varied depending on the parameters of sensing and the engine. Probe 14 is passivated with a very thin non-conductive coating or layer 17. This coating or layer 17 accounts for the lack of electrical shorting by the soot layer accumulated by probe 14 during operation of the engine. "Pacivate" may be similar to "passivate", although the term passivate and variants of it are used in the present description. The passivation material may be composed of SiN4, cerium and the like. The thickness of the passivation layer on probe 14 may be between 0.001 and 0.100 inch. A nominal thickness may be about 0.01 inch. The passivation layer may be achieved with the exposure of the probe to high exhaust gas temperatures or may be coated with such layer vie a material added to the engine fuel.

Figure 3:
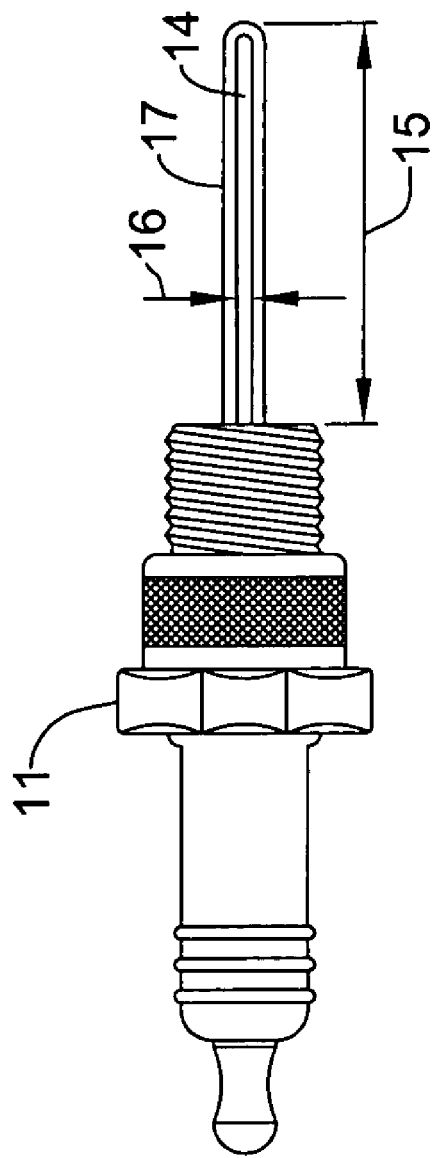
FIG. 3 is a side view of the PM sensor.

Sensor 10 with various dimensions is shown in FIG. 3. Examples of a length dimension 15 may be between 0.25 and 12 inches. A nominal value of dimension 15 may be about 3 to 4 inches. Examples of a thickness dimension 16 may be between 1/32" and 3/8". A nominal dimension 16 may be about 1/8".

An embodiment of sensor 10 may be a standard spark plug 11 (such as a Champion™ RJ19LM, though the model is not important) that has the outside electrode removed and has a 4 to 6 inch stainless steel extension 14 of about 1/8 inch diameter welded to the center electrode. Sensor 10 may be mounted in the exhaust stream 23 near the exhaust manifold 22 or after the turbocharger 19. The electrode 14 may be connected to a standard analog change amplifier in processor 26 to record charge transient 25 in the exhaust stream 23. The charge transients may be directly proportional to the soot (particulate) concentration in the exhaust stream 23. The extended electrode 14 may be passivated with a very thin non-conducting surface layer 17, so that the electrode 14 will develop an image charge from the exhaust particulates but will not be electrically shorted to the spark plug 11 base or the grounded exhaust pipe 18. The passivating layer 17 may be deposited or grown on the electrode 14. The 304 stainless steel may grow this passivating layer 17 spontaneously after a few minutes of operation in the exhaust stream 23 at elevated temperatures greater than 400 degrees C. (752 degrees F.). Other grades of stainless steel (e.g., 316) might not spontaneously grow the passivating layer 17. However, a passivating layer 17 of cerium oxide may be grown on these other grades of stainless steel by adding an organometalic cerium compound (about 100 ppm) to fuel for the engine 21.

Other methods of passivating the electrode 14 with a layer 17 may include sputter depositing refractory ceramic materials or growing oxide layers in controlled environments. The purpose of the passivating layer on electrode 14 is to prevent electrical shorts between the electrode 14 and the base of spark plug 11 due to particulate buildups, so that sensor 10 may retain its image charge monitoring activity of the exhaust stream 23. If electrode 14 did not have the passivating layer 17, sensor 10 may fail after a brief operating period because of a shorting of electrode 14 to the base of plug 11 due to a build up of conductive soot on the electrode 14.

Figure 5:
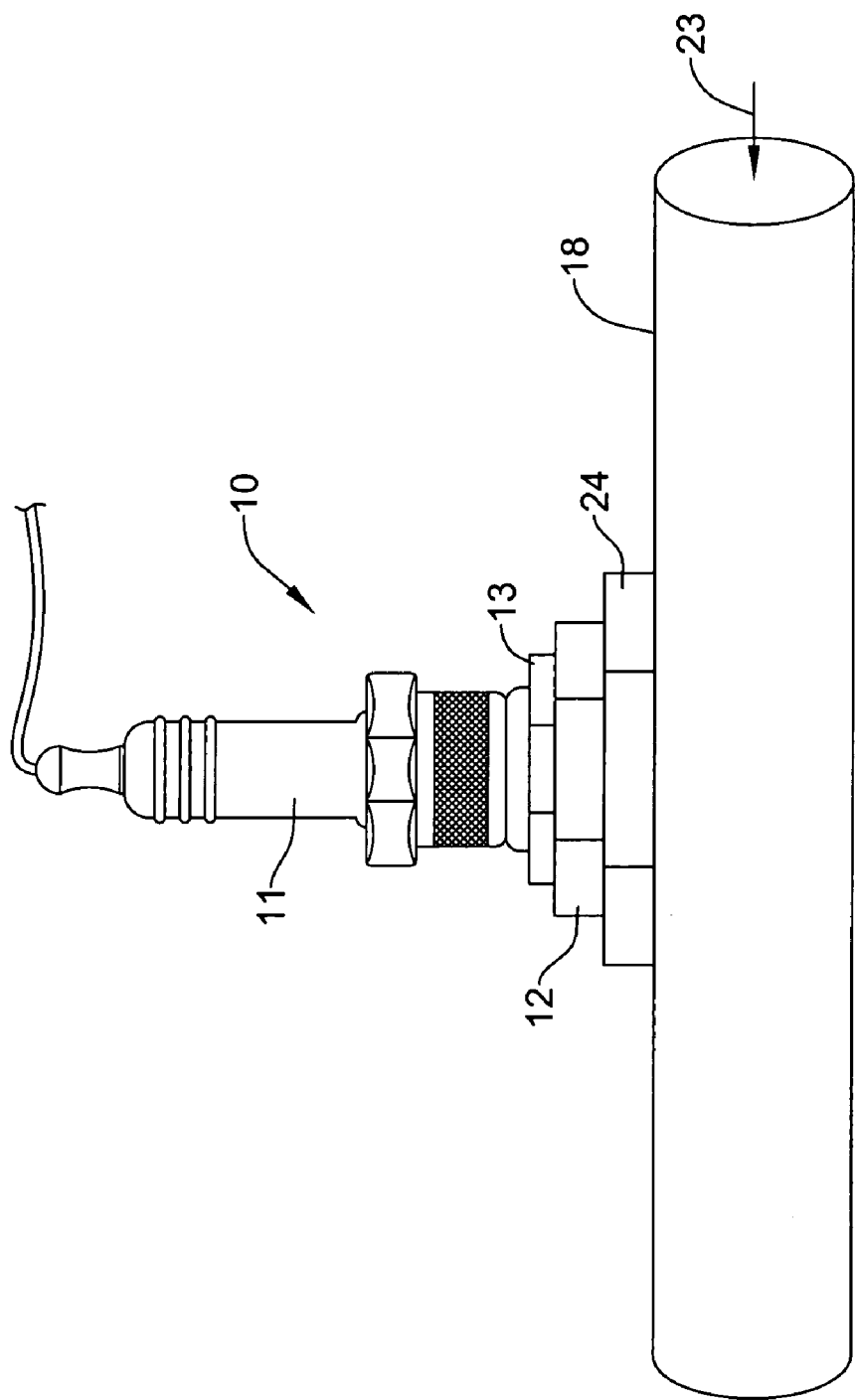
FIG. 5 shows an insertion of the PM sensor in an exhaust pipe.

FIG. 5 reveals an installation of sensor 10 in an exhaust pipe 18. There may be a stainless steel collar 24 welded into the exhaust pipe 18. Collar 24 may be fabricated with an oversized threaded access so that the sensor 10 could be easily changed with other sensors 10 having different probe styles. An adapting collar or insert 12 with external threads may fit the threaded collar 24 and internal threads may fit the threaded sensor 10. Adapting collar 12 may be made from stainless steel and Macor™, a machineable glass ceramic from Corning™. The Macor™ adaptors 12 may provide electrical and thermal connection or isolation of sensor 10 relative to exhaust pipe 18 or wherever collar 24 is mounted. Additional sensors 20 may be mounted in the exhaust manifold 22 upstream from turbocharger 19. Other sensors 30 may be mounted further down stream, e.g., about 2 meters, in exhaust pipe 18 from the turbocharger 19. The additional sensors 20 and 30 may allow one to examine the effects of the turbocharger 19, such as strong mixing, and residence time on a signal 25 from sensor 10. In the long term sites downstream from turbocharger 19 may be good locations because of the reduced risk of damage to the turbocharger 19 in the event of a sensor 10 failure.

Signals 25, indicating an amount of particulate matter in the exhaust 23, on the line from sensor 10 may go to a processor and/or controller 26. Processor 26 may be connected to other particulate sensors 20 and 30, engine sensors, and a fuel injection and intake manifold system 27. Based on signals 25 from sensor 10 and possibly from sensors 20 and 30, sensors in system 27 and engine 21, for sensing some or all of, but not limited to, the following engine parameters (via line 37 to processor 26) such as fuel flow, EGR (exhaust gas recirculation), injection timing, needle lift, crankshaft angle, cylinder pressure, valve position and lift, manifold vacuum, fuel/air mixture, the intake properties of air 28 and other information from or about engine 21, processor 26 may provide control information signals 29 to the fuel injection amount and timing, EGR percent, valve control, and intake manifold system 27, and the like, as desired, so as to cause engine 21 to expel a reduced amount of particulate emissions by adjusting fuel mixture, injection timing, percent EGR, valve control, and so forth. Incidentally, exhaust 23 may enter turbocharger 19 and cause a turbine 31 to spin and turn a compressor 32 via a shaft 33. Compressor 32 may compress incoming air 28 which goes in a more dense condition to system 27.

Initial concerns relative to sensor 10 were possible fouling by excessive soot and very high temperatures. However, operation of sensor 10 in an exhaust system has been reliable in view of operation of engine 21 under very heavy loads causing the observed exhaust 23 temperature to reach at least 670 degrees C. (1238 degrees F.) and resulting in a Bosch smoke number of exhaust 23 to be at least 5. The latter number may correspond to a particle mass concentration of 350 mg/m$^3$.

Sensor 10 may put out a reproducible rms signal representing its image charge monitoring of the exhaust 23, which is correlated to exhaust smoke as characterized by the Bosch smoke number. Sensor 10 generally does not degrade due to soot build-up over a long period of time. Also, sensor 10 does not appear to degrade at various temperatures.

Figure 6:
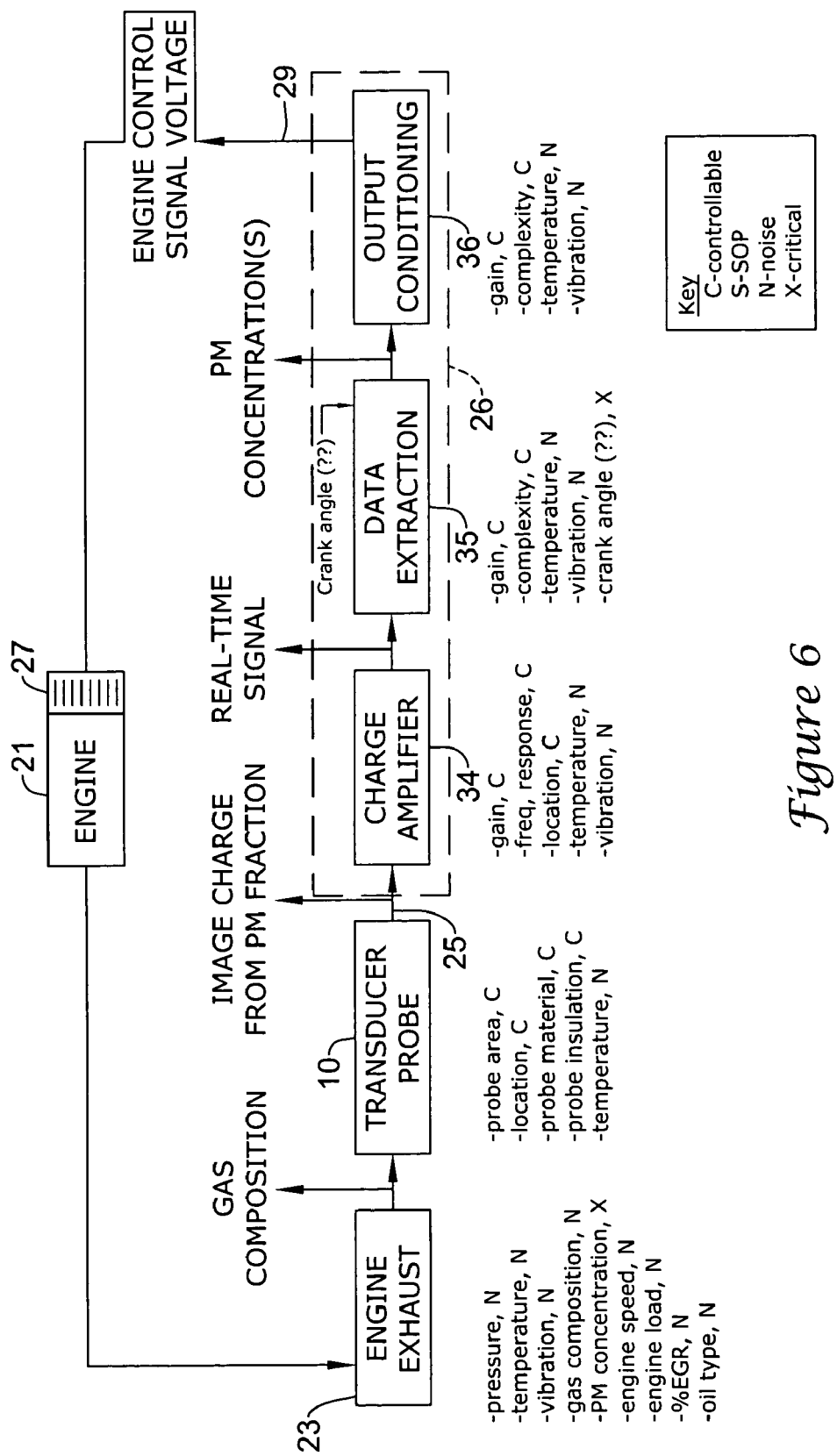
FIG. 6 is a loop for engine control based on parameters of an engine including the particulate matter of its exhaust emissions.

FIG. 6 is one version of a loop for engine control based on the particulate matter of the exhaust emissions. Engine 21 may output an exhaust 23 which is sensed by sensor 10 which in turn may output an image charge signal 25 to processor 26 which may include an amplifier 34, a data extractor 35, and an output signal conditioner 36, among other components of the processor. Signal 25 may go to a charge amplifier 34 which may output a real-time signal to a data extraction device 35 which may receive a crankshaft angle determination. Components 34, 35 and 36 may have other parameter inputs for improving engine control and performance. The output from device 35 may include an electronic indication of the PM concentration or concentrations. This signal may go to signal conditioning 36 which may, based on other various inputs of engine data (e.g., timing, temperature, percent EGR, valve position, other engine information) provide engine control voltage signals 29 (for engine timing, percent EGR, valve control, and the like) to the fuel injection and manifold system 27 of engine 21.

Although the invention has been described with respect to at least one illustrative embodiment, many variation and modifications will become apparent to those skilled in the art upon reading the present specification. It is therefore the intention that the appended claims be interpreted as broadly as possible in view of the prior art to include all such variations and modifications.

What is claimed is:

1. A particulate matter detector comprising:
a spark plug having a center electrode;
a rod attached to the center electrode; and
a passivation layer formed on the metal rod; and
wherein:
the rod is a metal rod;
the metal rod is a steel rod; and
the passivation layer is oxidized steel.

2. The detector of claim 1, wherein the steel is stainless steel.

3. The detector of claim 2, wherein the steel is 304 stainless steel.

4. The detector of claim 2 wherein:
the metal rod has a length between 0.25 inch and 12 inches; and
the metal rod has a thickness between 1/32 inch and 3/8 inch.

5. A method of making a particulate detector, comprising:
obtaining a spark plug having a center electrode;
attaching a metal rod to the center electrode; and
forming a passivating film on the metal rod; and
wherein:
the metal rod comprises stainless steel; and
the passivating film is oxidized stainless steel.

6. The method of claim 5, wherein the metal rod comprises 304 stainless steel.

7. A method of making a sensor, comprising:
forming an elongated piece of metal placing the elongated piece of metal in an insulator;
forming a terminal connected to the elongated piece of metal;
forming a thin film of insulation on the elongated piece of metal; and
wherein:
the elongated piece of metal is stainless steel; and
the film of insulation is formed by oxidizing the stainless steel.

8. A detector comprising:
a metal base;
an insulator situated in the metal base;
an elongated piece of metal situated in the insulator; and
an insulative film formed on the elongated piece of metal; and
wherein:
the elongated piece of metal comprises stainless steel; and
the insulative film is a forming of a passivating film from the stainless steel.

9. The detector of claim 8, wherein the elongated piece of metal comprises 304 stainless steel.

10. The detector of claim 9, wherein:
the elongated piece of metal is connected to an amplifier; and
the amplifier has an output that may indicate a concentration of particulate matter in a vicinity of the elongated piece of metal.

11. The detector of claim 10, wherein the elongated piece of metal is situated in an exhaust system of an engine.

12. The detector of claim 11, further comprising;
a processor comprising the amplifier; and
a plurality of sensors connected to the engine and the processor; and
wherein the processor provides control signals to the engine for affecting an amount of particulate matter in the exhaust system.

13. The detector of claim 12, wherein the control signals may affect fuel injection timing and percent of exhaust gas recirculation of the engine.

14. A detector comprising:
a base;
a probe situated in the base; and
a passivating film formed on the probe; and
wherein:
the passivating film is formed from a material of the probe;
the probe is connected to an amplifier; and
the amplifier has an output that may indicate a magnitude of charge of a concentration of particulate matter on the film of the probe.

15. The detector of claim 14, further comprising;
a processor comprising the amplifier; and
a plurality of sensors connected to an engine and the processor; and
wherein the processor provides control signals to the engine for affecting an amount of particulate matter in an exhaust system.

16. The detector of claim 15, wherein the control signals may affect fuel injection timing and percent of exhaust gas recirculation of the engine.

17. A detector comprising:
a supporting base; and
an electrode having a detecting portion and a non-detecting portion; and
wherein:
the non-detecting portion is situated in the supporting base;
a passivating film is formed on all of the detecting portion of the electrode; and
the electrode is for detecting particulate matter, in a vicinity of the electrode, which has a charge and attaches to the passivating film.

18. The detector of claim 17, wherein:
the electrode is connected to an amplifier; and
the amplifier has an output that may indicate a concentration of particulate matter in the vicinity of the electrode due to an input from the electrode of the charge of the particulate matter that attaches to the passivating layer.

19. The detector of claim 18, further comprising;
a processor comprising the amplifier; and
a plurality of sensors connected to an engine and the processor; and
wherein the processor provides control signals to the engine for affecting an amount of particulate matter in an exhaust system.

20. The detector of claim 19, wherein the control signals may affect fuel injection timing and percent of exhaust gas recirculation of the engine.

* * * * *